(12) United States Patent
Miyachi

(10) Patent No.: US 11,589,839 B2
(45) Date of Patent: Feb. 28, 2023

(54) ULTRASOUND DIAGNOSIS APPARATUS AND METHOD OF CONTROLLING ULTRASOUND DIAGNOSIS APPARATUS

(71) Applicant: FUJIFILM Corporation, Tokyo (JP)

(72) Inventor: Yukiya Miyachi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 19 days.

(21) Appl. No.: 16/826,714

(22) Filed: Mar. 23, 2020

(65) Prior Publication Data

US 2020/0214680 A1 Jul. 9, 2020

Related U.S. Application Data

(63) Continuation of application No. PCT/JP2018/021730, filed on Jun. 6, 2018.

(30) Foreign Application Priority Data

Sep. 27, 2017 (JP) .............................. JP2017-185946

(51) Int. Cl.
*A61B 8/08* (2006.01)
*A61B 8/00* (2006.01)

(52) U.S. Cl.
CPC .......... *A61B 8/5207* (2013.01); *A61B 8/0858* (2013.01); *A61B 8/42* (2013.01);
(Continued)

(58) Field of Classification Search
CPC ........... A61B 8/0858; A61B 8/14; A61B 8/42; A61B 8/4245; A61B 8/4263;
(Continued)

(56) References Cited

U.S. PATENT DOCUMENTS

2009/0124903 A1   5/2009  Osaka
2011/0137169 A1   6/2011  Akaki et al.
(Continued)

FOREIGN PATENT DOCUMENTS

CN    101060813 A    10/2007
CN    106659474 A    5/2017
(Continued)

OTHER PUBLICATIONS

Extended European Search Report for corresponding European Application No. 18860807.9, dated Oct. 12, 2020.
(Continued)

*Primary Examiner* — Joseph M Santos Rodriguez
*Assistant Examiner* — Maria Christina Talty
(74) *Attorney, Agent, or Firm* — Birch, Stewart, Kolasch & Birch, LLP

(57) ABSTRACT

An ultrasound diagnosis apparatus including: an ultrasound probe; a processor configured to perform transmission of ultrasound beam from the ultrasound probe to a subject to acquire an ultrasound image; a camera configured to acquire a digital image of a state of the ultrasound probe being in contact with the subject; a touch panel including a display screen displaying the ultrasound image and the digital image; an interface to receive instruction to acquire the ultrasound image and/or the digital image from a user; and a memory configured to store the ultrasound image and the digital image, wherein the processor is further configured to: exclusively control between the acquisition of the ultrasound image and the acquisition of the digital image according to instruction received by the interface; and save the ultrasound image and the digital image of the same inspection in the memory in association with each other.

22 Claims, 13 Drawing Sheets

(52) U.S. Cl.
CPC ............ *A61B 8/4444* (2013.01); *A61B 8/461* (2013.01); *A61B 8/54* (2013.01)

(58) Field of Classification Search
CPC ....... A61B 8/4444; A61B 8/461; A61B 8/463; A61B 8/5207; A61B 8/5246; A61B 8/5292; A61B 8/54
See application file for complete search history.

(56) References Cited

U.S. PATENT DOCUMENTS

| | | | |
|---|---|---|---|
| 2012/0179039 A1 | 7/2012 | Pelissier et al. | |
| 2013/0102903 A1* | 4/2013 | Tanaka | A61B 8/4444 600/447 |
| 2014/0121524 A1* | 5/2014 | Chiang | G16H 40/67 600/459 |
| 2014/0171797 A1* | 6/2014 | Hershey | A61B 8/4245 600/437 |
| 2015/0164479 A1* | 6/2015 | Toji | A61B 8/5207 600/440 |
| 2105/0164479 | 6/2015 | Toji | |
| 2016/0004330 A1* | 1/2016 | Sundaran Baby Sarojam | A61B 8/467 345/157 |
| 2016/0026894 A1* | 1/2016 | Nagase | A61B 8/5207 600/443 |
| 2016/0171702 A1* | 6/2016 | Wittmeier | G06T 7/74 382/103 |
| 2016/0206283 A1* | 7/2016 | Ota | A61B 8/469 |
| 2016/0361043 A1* | 12/2016 | Kim | A61B 8/0808 |
| 2017/0215842 A1 | 8/2017 | Ryu et al. | |
| 2017/0252002 A1* | 9/2017 | Mine | A61B 8/4218 |

FOREIGN PATENT DOCUMENTS

| | | |
|---|---|---|
| JP | 2000-201926 A | 7/2000 |
| JP | 2001-112752 A | 4/2001 |
| JP | 2005-58577 A | 3/2005 |
| JP | 2006-400 A | 1/2006 |
| JP | 4469444 B2 * | 5/2010 |
| JP | 2015-131099 A | 7/2015 |

OTHER PUBLICATIONS

International Preliminary Report on Patentability and Written Opinon of the International Searching Authority dated Apr. 9, 2020, for International Application No. PCT/JP2018/021730, with an English Translation.

International Search Report, dated Aug. 28, 2018, for International Application No. PCT/JP2018/021730, with an English translation.

Chinese Office Action and Search Report for corresponding Chinese Application No. 201880062749.5, dated Mar. 23, 2022, with English translation.

* cited by examiner

ULTRASOUND DIAGNOSIS APPARATUS AND METHOD OF CONTROLLING ULTRASOUND DIAGNOSIS APPARATUS

CROSS-REFERENCE TO RELATED APPLICATIONS

This application is a Continuation of PCT International Application No. PCT/JP2018/021730 filed on Jun. 6, 2018, which claims priority under 35 U.S.C § 119(a) to Japanese Patent Application No. 2017-185946 filed on Sep. 27, 2017. Each of the above applications is hereby expressly incorporated by reference, in its entirety, into the present application.

BACKGROUND OF THE INVENTION

1. Field of the Invention

The present invention relates to an ultrasound diagnosis apparatus and a method of controlling an ultrasound diagnosis apparatus, and in particular, to an ultrasound diagnosis apparatus capable of acquiring a digital image and a method of controlling an ultrasound diagnosis apparatus.

2. Description of the Related Art

Hitherto, as an apparatus that obtains an image of the inside of a subject, an ultrasound diagnosis apparatus is known. In general, the ultrasound diagnosis apparatus transmits an ultrasonic beam from a transducer array, in which a plurality of elements are arranged, toward the subject and receives an ultrasound echo from the subject in the transducer array to acquire element data. In addition, the ultrasound diagnosis apparatus electrically processes the acquired element data, thereby being able to acquire an ultrasound image in which a part of the subject is reflected.

In a case of performing inspection on the subject using such an ultrasound diagnosis apparatus, a user often observes an ultrasound image saved during inspection again after inspection ends. In this case, the user may hardly determine a part of the subject, with which the ultrasound probe is brought into contact in capturing the ultrasound image observed again, only by confirming the ultrasound image. For this reason, various studies have been made in the ultrasound diagnosis apparatus such that a contact position of the ultrasound probe with the subject in a case where the ultrasound image is captured can be easily confirmed by the user.

For example, JP2000-201926A discloses an ultrasound diagnosis apparatus that displays a three-dimensional body mark on a display unit along with an acquired ultrasound image and further displays a probe mark on the displayed body mark. The body mark that is displayed along with the ultrasound image and the probe mark that is displayed on the body mark are selected by a user. Furthermore, the ultrasound diagnosis apparatus disclosed in JP2000-201926A can also capture digital images of a subject and an ultrasound probe and display the captured digital images of the subject and the ultrasound probe on the display unit instead of the body mark and the probe mark.

SUMMARY OF THE INVENTION

However, in the ultrasound diagnosis apparatus disclosed in JP2000-201926A, in capturing the digital images displayed instead of the body mark and the probe mark, the acquisition timing of the ultrasound image needs to coincide with the acquisition timing of the digital image. For this reason, the user needs an imaging position of the digital image while confirming a contact position of the ultrasound probe with the subject, such as freeze-displaying the ultrasound image on the display unit in conformity with a timing of capturing the digital image. Accordingly, it is difficult to adjust both of a position of the ultrasound probe and the imaging position of the digital image to appropriate positions. That is, it is difficult to achieve both of acquisition of an appropriate ultrasound image and acquisition of an appropriate digital image corresponding to the ultrasound image. For this reason, the user hardly clearly confirm a state in which the ultrasound probe is in contact with the part of the subject with reference to the digital image captured corresponding to the ultrasound image, and hardly performs accurate diagnosis only by referring to digital image along with the ultrasound image.

The invention has been accomplished in order to solve such a problem in the related art, and an object of the invention is to an ultrasound diagnosis apparatus and a method of controlling an ultrasound diagnosis apparatus capable of allowing a user to perform more accurate diagnosis while referring to an ultrasound image and a digital image.

In order to achieve the above-described object, the invention provides an ultrasound diagnosis apparatus comprising: an ultrasound probe; a processor configured to perform transmission of ultrasound beam from the ultrasound probe to a subject to acquire an ultrasound image; a camera configured to acquire a digital image of a state of the ultrasound probe being in contact with the subject; a touch panel configured to include a display screen displaying the ultrasound image and the digital image; an interface configured to receive an instruction to acquire the ultrasound image and/or the digital image from a user; and a memory configured to store the ultrasound image and the digital image, wherein the camera is further configured to acquire the digital image in a first direction opposite to a second direction to which the display screen of the touch panel is directed, wherein the processor is further configured to: exclusively control between the acquisition of the ultrasound image and the acquisition of the digital image according to the instruction received from the interface, and save the ultrasound image and the digital image of the same inspection in the memory in association with each other, and wherein the processor is further configured to cause the camera to acquire the digital image in accordance with the instruction received from the interface only in a case where the ultrasound image is freeze-displayed on the display screen.

The ultrasound image operation section and the digital image operation section may be displayed on the display screen of the touch panel. The save controller may save the ultrasound image in association with a time at which the ultrasound image is acquired and saves the digital image in association with a time at which the digital image is acquired.

The save controller may save the ultrasound image freeze-displayed on the display screen of the touch panel and the digital image acquired by the digital image acquisition unit during the freeze display of the ultrasound image in association with each other. The save controller may save an ultrasound image acquired by the ultrasound image acquisition unit in a period until a digital image is newly acquired by the digital image acquisition unit further in association with the digital image acquired by the digital image acquisition unit during the freeze display of the ultrasound image.

The ultrasound diagnosis apparatus may further comprise a probe detection unit that detects a position of the ultrasound probe based on the digital image. The probe detection unit may detect the position of the ultrasound probe based on color information of the digital image.

The ultrasound diagnosis apparatus may further comprise a trimming unit that generates a trimmed image by cutting a peripheral portion of the position of the ultrasound probe detected by the probe detection unit from the digital image, and the save controller may save the trimmed image generated by the trimming unit as the digital image in association with the ultrasound image.

The ultrasound diagnosis apparatus may further comprise a part estimation unit that estimates, based on the digital image, a part of the subject where the ultrasound image is acquired, and a marking unit that attaches a body mark corresponding to the part estimated by the part estimation unit to the ultrasound image. The marking unit may attach a probe mark to the ultrasound image along with the body mark based on the position of the ultrasound probe detected by the probe detection unit.

The part estimation unit may estimate the part of the subject in consideration of at least one of an inspection part name input by the user corresponding to the inspection or the ultrasound image. The part estimation unit may detect a skin region from the digital image based on color information of the digital image and may estimate the part of the subject based on the detected skin region and the position of the ultrasound probe detected by the probe detection unit.

The invention also provides a method of controlling an ultrasound diagnosis apparatus comprising a touch panel. The method comprises performing transmission and reception of an ultrasonic beam from an ultrasound probe to a subject and imaging a reception signal output from the ultrasound probe to acquire an ultrasound image, imaging a state of the ultrasound probe being in contact with the subject in a visual field in a direction opposite to a direction, to which a display screen of the touch panel is directed, to acquire a digital image, displaying the ultrasound image and the digital image on the touch panel, saving the ultrasound image and the digital image acquired in the same inspection in association with each other, and enabling the acquisition of the digital image only in a case where the ultrasound image is freeze-displayed and exclusively performing the acquisition of the ultrasound image and the acquisition of the digital image.

According to the invention, the ultrasound diagnosis apparatus comprises the operation controller that makes the digital image operation section operable by the user only in a case where the ultrasound image is freeze-displayed and exclusively operates the ultrasound image acquisition unit and the digital image acquisition unit based on the operations of the ultrasound image operation section and the digital image operation section, and the save controller that saves the ultrasound image and the digital image acquired in the same inspection in the image memory in association with each other. For this reason, it is possible to allow the user to perform more accurate diagnosis while referring to the ultrasound image and the digital image.

DESCRIPTION OF THE PREFERRED EMBODIMENTS

Hereinafter, an embodiment of the invention will be described referring to the accompanying drawings.

Embodiment 1

Figure 1:
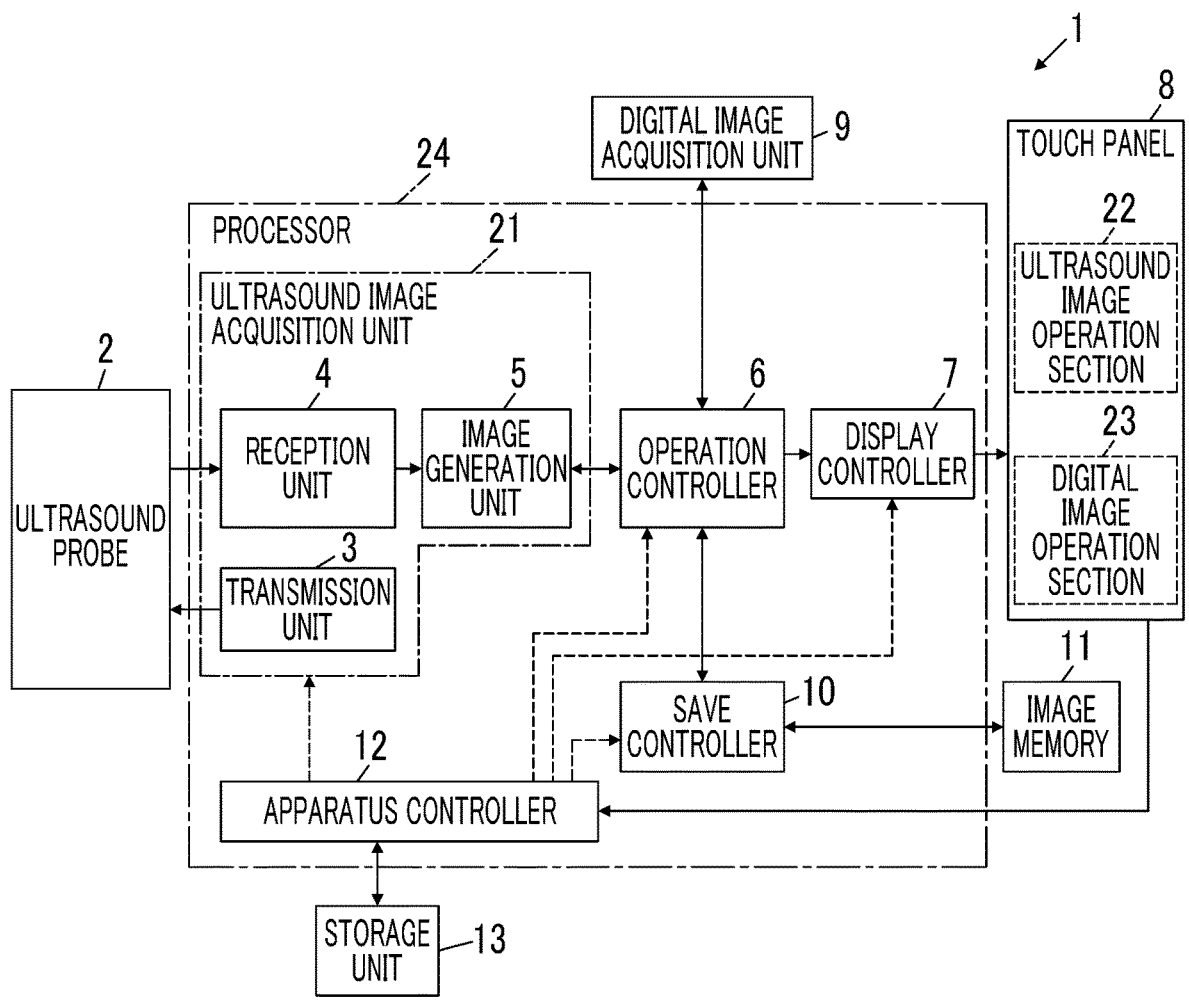
FIG. 1 is a block diagram showing the configuration of an ultrasound diagnosis apparatus according to Embodiment 1 of the invention.

FIG. 1 shows the configuration of an ultrasound diagnosis apparatus 1 according to Embodiment 1 of the invention. As shown in FIG. 1, the ultrasound diagnosis apparatus 1 comprises an ultrasound probe 2, and a transmission unit 3 and a reception unit 4 are connected to the ultrasound probe 2. An image generation unit 5, an operation controller 6, a display controller 7, and a touch panel 8 are sequentially connected to the reception unit 4. A digital image acquisition unit 9 and a save controller 10 are connected to the operation controller 6. An image memory 11 is connected to the save controller 10. Here, the transmission unit 3, the reception unit 4, and the image generation unit 5 constitute an ultrasound image acquisition unit 21. The touch panel 8 includes an ultrasound image operation section (an ultrasound image operation interface) 22 and a digital image operation section (a digital image operation interface) 23. An apparatus controller 12 is connected to the operation controller 6, the display controller 7, the touch panel 8, the save controller 10, and the ultrasound image acquisition unit 21, and a storage unit 13 is connected to the apparatus controller 12.

The operation controller 6, the display controller 7, the save controller 10, the apparatus controller 12, and the ultrasound image acquisition unit 21 constitute a processor 24. The operation controller 6 and the digital image acquisition unit 9, the operation controller 6 and the save controller 10, the operation controller 6 and the ultrasound image acquisition unit 21, the save controller 10 and the image memory 11, and the apparatus controller 12 and the storage unit 13 are connected to deliver information to each other in both directions, respectively.

The ultrasound probe 2 shown in FIG. 1 has a transducer array, and the transducer array has a plurality of elements (ultrasound transducers) arranged in a one-dimensional or two-dimensional manner. Each element transmits an ultrasonic wave in response to an actuation signal supplied from the transmission unit 3, receives a reflected wave from a subject, and outputs a reception signal. Each element is constituted of a transducer in which electrodes are formed at both ends of a piezoelectric body made of, for example, piezoelectric ceramic represented by lead zirconate titanate (PZT), a polymer piezoelectric element represented by poly vinylidene di fluoride (PVDF), piezoelectric single crystal represented by a lead magnesium niobate-lead titanate (PMN-PT), or the like.

The transmission unit 3 of the ultrasound image acquisition unit 21 includes, for example, a plurality of pulse generators, and adjusts an delay amount of each actuation signal based on a transmission delay pattern selected in response to a control signal from the apparatus controller 12 such that ultrasonic waves transmitted from a plurality of elements in the transducer array of the ultrasound probe 2 form an ultrasonic beam and supplies the actuation signals to a plurality of elements. In this way, in a case where a pulsed or continuous-wave voltage is applied to the electrodes of each of the elements of the transducer array, the piezoelectric body expands and contracts to generate pulsed or continuous-wave ultrasonic waves from the respective transducers. An ultrasonic beam is formed from a combined wave of the ultrasonic waves.

The transmitted ultrasonic beam is reflected by, for example, a target, such as a part of the subject, and propagates toward the transducer array of the ultrasound probe 2. The ultrasonic waves propagating toward the transducer array in this way are received by the respective elements constituting the transducer array. In this case, the respective elements expand and contract with reception of the propagating ultrasonic waves to generate electrical signals. The electrical signals are output from the respective elements to the reception unit 4 as reception signals of the ultrasonic waves.

Figure 2:
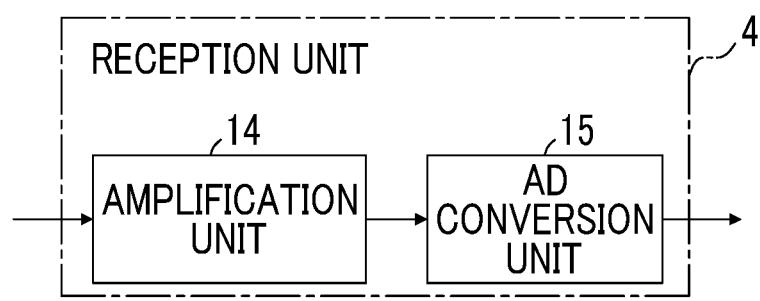
FIG. 2 is a block diagram showing the internal configuration of a reception unit in Embodiment 1 of the invention.
Figure 3:
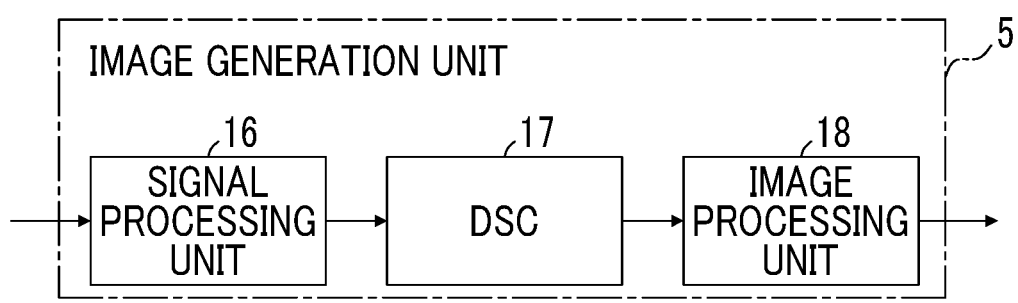
FIG. 3 is a block diagram showing the internal configuration of an image generation unit in Embodiment 1 of the invention.

As shown in FIG. 2, the reception unit 4 of the ultrasound image acquisition unit 21 has a configuration in which an amplification unit 14 and an analog-to-digital (AD) conversion unit 15 are connected in series. The amplification unit 14 amplifies the reception signals of the ultrasonic waves input from the respective elements constituting the transducer array of the ultrasound probe 2 and transmits the amplified reception signals to the AD conversion unit 15. The AD conversion unit 15 converts the reception signals transmitted from the amplification unit 14 to digital element data and outputs the element data to the image generation unit 5. As shown in FIG. 3, the image generation unit 5 of the ultrasound image acquisition unit 21 has a configuration in which a signal processing unit 16, a digital scan converter (DSC) 17, and an image processing unit 18 are connected in series.

The digital image acquisition unit 9 of the ultrasound diagnosis apparatus 1 images a state of the ultrasound probe 2 being in contact with the subject to acquire a digital image. As the digital image acquisition unit 9, a digital camera that is incorporated in the ultrasound diagnosis apparatus 1 can be used.

The operation controller 6 of the processor 24 brings the digital image operation section 23 into a state operable by the user only in a case where an ultrasound image generated by the image generation unit 5 is freeze-displayed on a display screen of the touch panel 8 and exclusively operates the ultrasound image acquisition unit 21 and the digital image acquisition unit 9 based on user's operations of the ultrasound image operation section 22 and the digital image operation section 23. Here, the freeze display refers to that, in a case where the ultrasound images are sequentially acquired by the ultrasound image acquisition unit 21 and are sequentially displayed as a moving image on the display screen of the touch panel 8, the display as the moving image is stopped, and a still ultrasound image is displayed. The freeze display is display that is generally performed in various ultrasound diagnosis apparatuses. Exclusively operating the ultrasound image acquisition unit 21 and the digital image acquisition unit 9 refers to that, in a case where one of the ultrasound image acquisition unit 21 and the digital image acquisition unit 9 is operated, the other unit is not operated.

The touch panel 8 of the ultrasound diagnosis apparatus 1 is a device that has the display screen, on which the ultrasound image acquired by the ultrasound image acquisition unit 21 and the digital image acquired by the digital image acquisition unit 9 are displayed, and allows the user to perform a touch operation. The display screen of the touch panel 8 is constituted, for example, by disposing a so-called touch sensor on a display device, such as a liquid crystal display (LCD). In a case where a touch operation is performed from the user through the touch panel 8, a signal of the touch operation is output to the apparatus controller 12, and the apparatus controller 12 controls the respective units of the ultrasound diagnosis apparatus 1 based on the output signal of the touch operation.

The touch panel 8 has an ultrasound image operation section 22 and a digital image operation section 23. The ultrasound image operation section 22 is configured to receive an instruction from the user to acquire the ultrasound image by the ultrasound image acquisition unit 21. The digital image operation section 23 is configured to receive an instruction from the user to acquire the digital image by the digital image acquisition unit 9. Specifically, the ultrasound image operation section 22 and the digital image operation section 23 are displayed on the display screen of the touch panel 8, and are operated when being touched by the user.

The ultrasound image operation section 22 includes an input section or the like that allows the user to perform the freeze display of the ultrasound image on the display screen of the touch panel 8, saving of the ultrasound image, setting of imaging conditions, such as brightness, contrast, and a dynamic range, in imaging a part of the subject, and the like. The digital image operation section 23 includes, for example, an operation button or the like that is provided for the operation of the digital image acquisition unit 9, imaging of the subject, saving of the digital image, and the like.

The save controller 10 of the processor 24 saves the ultrasound image and the digital image acquired in the same inspection in the image memory 11 in association with each other. For example, the save controller 10 can save the ultrasound image freeze-displayed on the display screen of the touch panel 8 and the digital image acquired by the digital image acquisition unit 9 during the freeze display of the ultrasound image in the same inspection in association with each other.

The image memory 11 of the ultrasound diagnosis apparatus 1 saves the ultrasound image and the digital image associated with each other by the save controller 10, and a recording medium, such as a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), can be used.

In order to secure confidentiality relating to information of the subject, it is preferable that image memory 11 is not read from an external device. For this reason, it is preferable that a recording medium connectable to an external device, such as a server, is not used as the image memory 11.

The apparatus controller 12 of the processor 24 controls the respective units of the ultrasound diagnosis apparatus 1 based on commands input from the user through the ultrasound image operation section 22, the digital image operation section 23, and the like of the touch panel 8, and an operation program stored in the storage unit 13 described below. The display controller 7 of the processor 24 displays the ultrasound image acquired by the ultrasound image acquisition unit 21, the digital image acquired by the digital image acquisition unit 9, the ultrasound image and the digital image read from the image memory 11, and the like on the display screen of the touch panel 8 under the control of the apparatus controller 12.

The storage unit 13 of the ultrasound diagnosis apparatus 1 stores the operation program of the processor 24, and a recording medium, such as an HDD, an SSD, an FD, an MO disc, an MT, a RAM, a CD, a DVD, an SD card, or a USB memory, a server, or the like can be used. The operation program is distributed in a form of being recorded on the above-described recording medium, and is installed on the processor 24 from the recording medium. Alternatively, the operation program is stored in a server or the like connected to a network in a state accessible from the outside, is downloaded to the processor 24 on demand, and is installed.

The processor 24 constituted of the transmission unit 3, the reception unit 4, the image generation unit 5, the operation controller 6, the display controller 7, the save controller 10, and the apparatus controller 12 is constituted of a central processing unit (CPU) and the operation program causing the CPU to execute various kinds of processing; however, the units may be constituted of digital circuits. The transmission unit 3, the reception unit 4, the image generation unit 5, the operation controller 6, the display controller 7, the save controller 10, and the apparatus controller 12 constituting the processor 24 may be integrated partially or entirely in one CPU. As the CPU executes the operation program, the CPU functions as the transmission unit 3, the reception unit 4, the image generation unit 5, the operation controller 6, the display controller 7, the save controller 10, and the apparatus controller 12.

Figure 4:
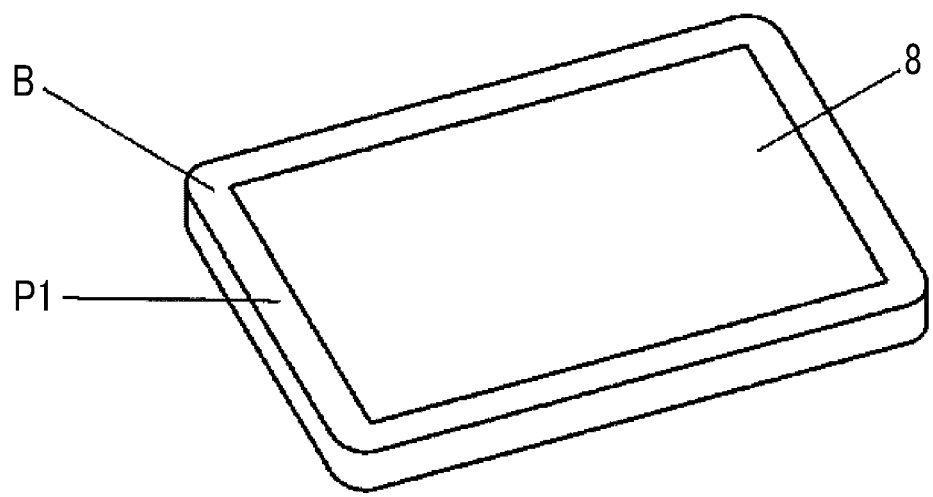
FIG. 4 is a perspective view when viewing a front surface side of the ultrasound diagnosis apparatus body in Embodiment 1 of the invention.
Figure 5:
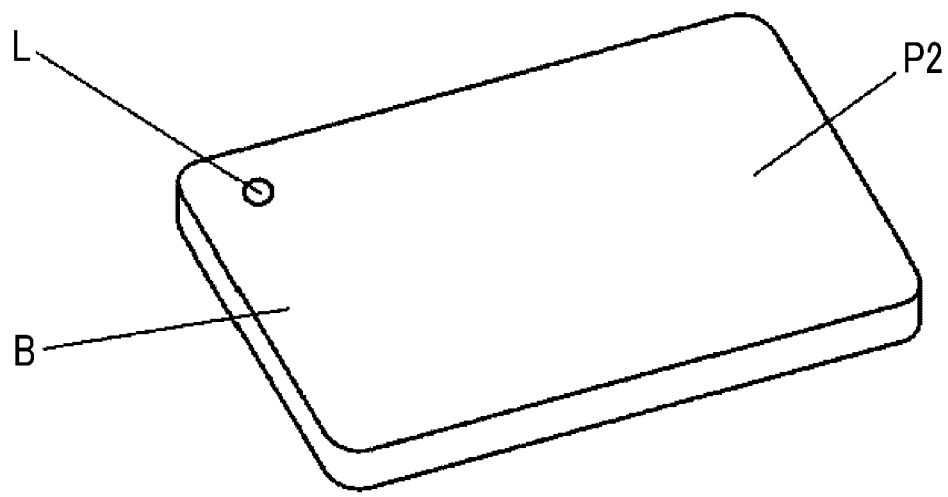
FIG. 5 is a perspective view when viewing a rear surface side of the ultrasound diagnosis apparatus body in Embodiment 1 of the invention.

Here, the ultrasound diagnosis apparatus 1 having the above-described configuration can be constituted of, for example, an ultrasound diagnosis apparatus body B shown in FIGS. 4 and 5 that is portable by the user, and the ultrasound probe 2 (not shown) that is connected to the ultrasound diagnosis apparatus body B. In this case, though not shown, the ultrasound diagnosis apparatus body B is incorporated with the touch panel 8, the digital image acquisition unit 9, the image memory 11, the storage unit 13, and the processor 24. In the ultrasound diagnosis apparatus body B, as shown in FIG. 4, the display screen of the touch panel 8 is disposed on a front surface P1, and as shown in FIG. 5, a camera lens L of the digital image acquisition unit 9 is disposed on a rear surface P2. Since the ultrasound diagnosis apparatus body B has such a configuration, the digital image acquisition unit 9 can acquire a digital image in a visual field in a direction opposite to a direction, to which the display screen of the touch panel 8 is directed.

Figure 6:
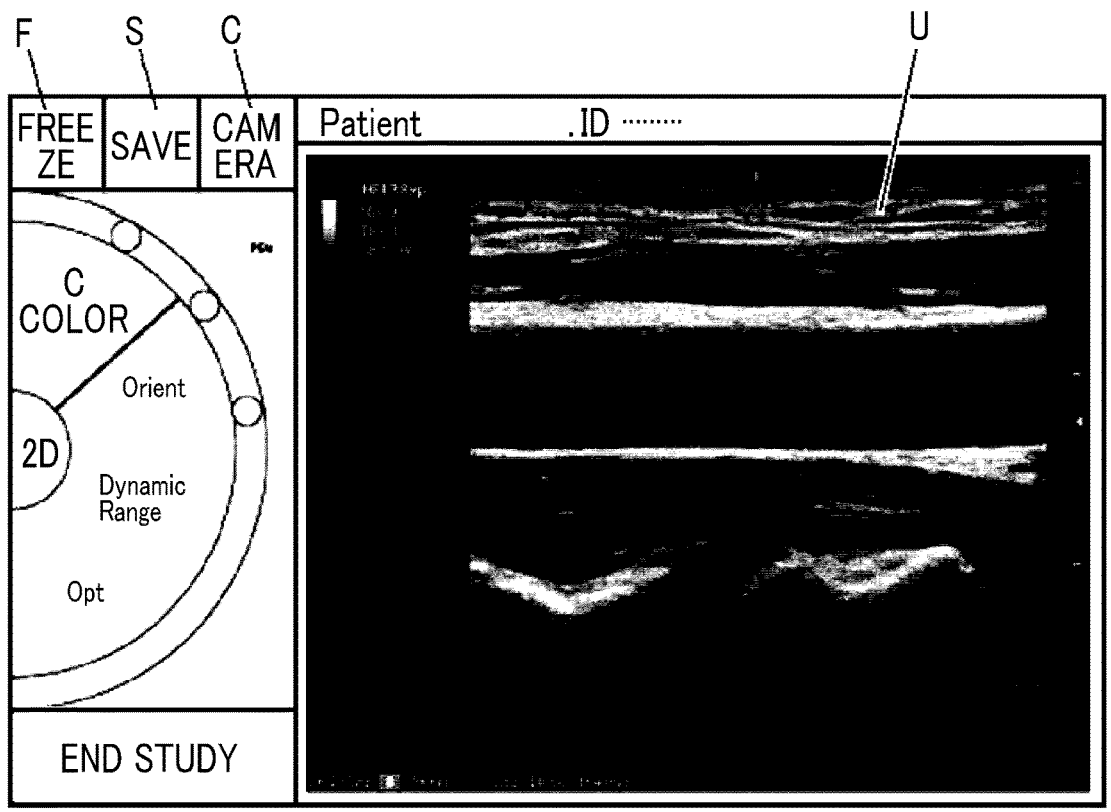
FIG. 6 is a display example of an ultrasound image acquired in Embodiment 1 of the invention.

Next, an operation of the ultrasound diagnosis apparatus 1 in Embodiment 1 of the invention will be described referring to FIGS. 6 to 9. First, the user brings the ultrasound probe 2 into contact with a part of the subject to capture an ultrasound image. With this, the ultrasound image acquired by the ultrasound image acquisition unit 21 is displayed as a moving image on the display screen of the touch panel 8. In this case, for example, display shown in FIG. 6 is performed on the display screen of the touch panel 8. In the example shown in FIG. 6, a freeze button F, a save button S, a camera button C, and ultrasound images U are displayed on the display screen of the touch panel 8.

Here, the save button S is shared by the ultrasound image operation section 22 and the digital image operation section 23, and is used as a part of the ultrasound image operation section 22, that is, a button for saving an ultrasound image or a part of the digital image operation section 23, that is, a button for saving a digital image based on the user's operations of the ultrasound image operation section 22 and the digital image operation section 23. In a case where a function of acquiring the ultrasound image U is operated, that is, in a case where the display shown in FIG. 6 is performed on the display screen of the touch panel 8, the ultrasound image operation section 22 includes the freeze button F and the save button S, and the digital image operation section 23 includes the camera button C.

In a state in which the ultrasound image U is displayed as a moving image on the display screen, the operation controller 6 brings the save button S and the camera button C into a state inoperable by the user. Specifically, the operation controller 6 can bring the save button S and the camera button C into a state of not responding to a user's touch operation.

In a case where the freeze button F is touched by the user, the ultrasound image U of a frame displayed on the display screen is freeze-displayed. In a case where the ultrasound image U is freeze-displayed, the operation controller 6 brings the save button S and the camera button C into a state operable by the user, that is, a state of responding to the user's touch operation. Here, in a case where the user touches the save button S, the ultrasound image U freeze-displayed on the display screen of the touch panel 8 is saved in the image memory 11. In a case where the user touches the camera button C, the digital image acquisition unit 9 is operated.

Figure 7:
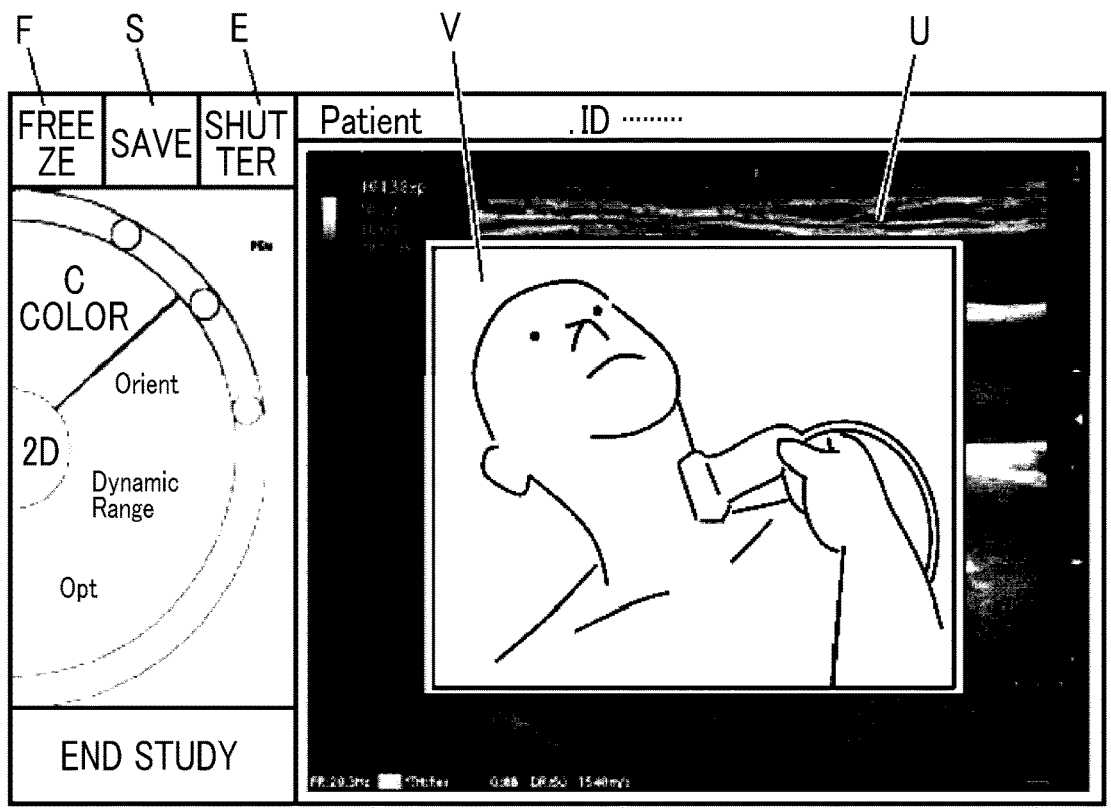
FIG. 7 is a display example of a digital image acquired in Embodiment 1 of the invention.

In a case where the digital image acquisition unit 9 is operated, as shown in FIG. 7, video V passing through the camera lens L is displayed on the display screen of the touch panel 8 in such a manner as to be superimposed on the freeze-displayed ultrasound image U, and a shutter button E is displayed instead of the camera button C. In this case, the digital image operation section 23 includes the save button S and the shutter button E, and the ultrasound image operation section 22 includes the freeze button F.

In a case where the user touches the shutter button E, video V at the time when the shutter button E is touched is taken as a digital image, which is a still image, and is displayed on the display screen of the touch panel 8. In this case, for example, the user fixes the visual field of the digital image acquisition unit 9 at a position easy to confirm that the ultrasound probe 2 is in contact with the part of the subject and touches the shutter button E. In a case where the digital image is displayed on the display screen of the touch panel 8, the operation controller 6 brings the save button S into a state operable by the user. Here, in a case where the user touches the save button S, the save controller 10 saves the digital image in the image memory 11 in association with the ultrasound image U freeze-displayed on the display screen of the touch panel 8.

Figure 8:
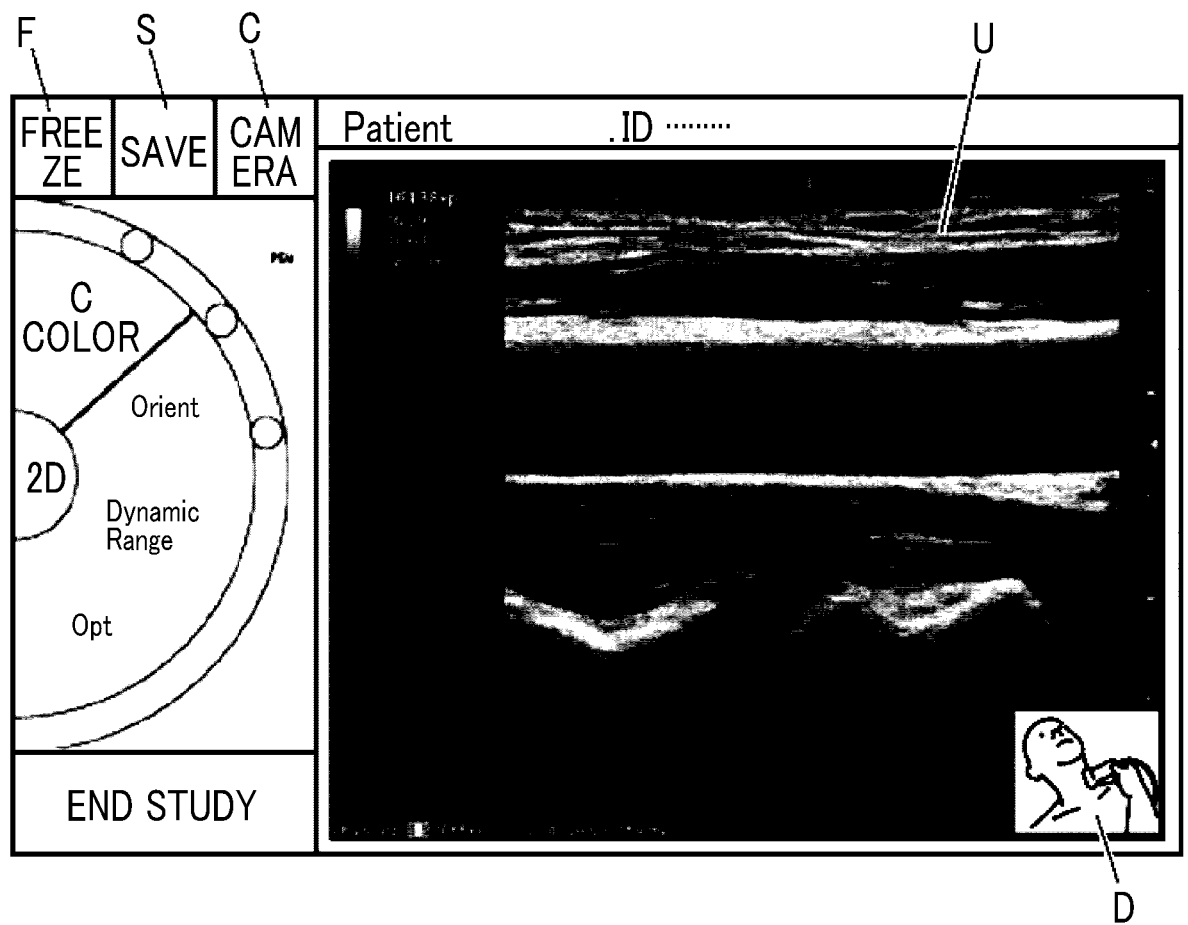
FIG. 8 is a diagram showing an example where the digital image acquired in Embodiment 1 of the invention is displayed in such a manner as to be superimposed on the ultrasound image.

In a case where the digital image is stored in the image memory 11, as shown in FIG. 8, a digital image D saved in the image memory 11 is reduced and displayed in an end portion of the ultrasound image U in a superimposed manner. In this case, the freeze display of the ultrasound image U is released, the ultrasound image U is displayed as a moving image on the display screen, and the camera button C is displayed instead of the shutter button E. In this way, the reduced digital image D is displayed in such a manner as to be superimposed on the ultrasound image U displayed as a moving image, whereby it is possible to allow the user to adjust a contact position of the ultrasound probe 2 with the subject while confirming the digital image D. In a case where such display is performed on the display screen of the touch panel 8, the ultrasound image operation section 22 includes the freeze button F and the save button S, the digital image operation section 23 includes the camera button C, and the camera button C is returned into a state inoperable by the user by the operation controller 6.

In this way, in a state in which the ultrasound image U is displayed as a moving image on the display screen of the touch panel 8, in a case where the freeze button F is touched by the user, the ultrasound image U is freeze-displayed, and in a case where the save button S is touched by the user, the freeze-displayed ultrasound image U is newly saved in the image memory 11. In addition, in a case where the camera button C is touched by the user, in a state in which the digital image D is displayed as a moving image on the display screen, in a case where the shutter button E is touched by the user, the digital image D at the time when the shutter button E is touched is saved in the image memory 11 in association with the newly saved ultrasound image U.

Figure 9:
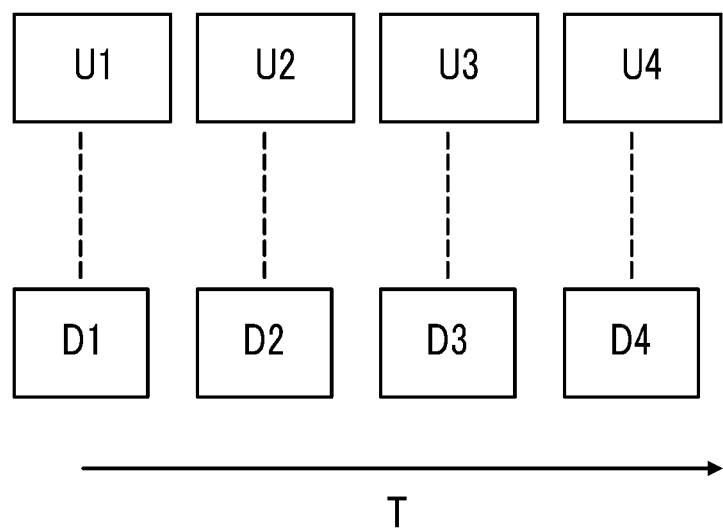
FIG. 9 is a conceptual diagram showing the correspondence relationship between the ultrasound image and the digital image associated with each other in Embodiment 1 of the invention.

In this way, the ultrasound image U freeze-displayed on the display screen of the touch panel 8 and the digital image D acquired by the digital image acquisition unit 9 during the freeze display of the ultrasound image U are saved in association with each other by the save controller 10, whereby it is possible to obtain the ultrasound image U and the digital image D having a correspondence relationship shown in FIG. 9. In FIG. 9, U1, U2, U3, and U4 indicate ultrasound images saved in the image memory 11, D1, D2, D3, and D4 indicate digital images saved in the image memory 11 in association with the ultrasound images U1, U2, U3, and U4 by the save controller 10, respectively, and the ultrasound images U1, U2, U3, and U4 and the digital images D1, D2, D3, and D4 are arranged along an imaging time T.

With the above, first, the operation controller 6 can bring the digital image operation section 23 into a state operable by the user only in a case where the ultrasound image U is freeze-displayed on the display screen of the touch panel 8, and can exclusively operate a function of acquiring the ultrasound image U and a function of acquiring the digital image D, that is, the ultrasound image acquisition unit 21 and the digital image acquisition unit 9 based on the user's operations of the ultrasound image operation section 22 and the digital image operation section 23. For this reason, the user can acquire the ultrasound image U by bringing the ultrasound probe 2 into contact with a part of the subject to be inspected at an appropriate position and can acquire the appropriate digital image D by fixing the digital image acquisition unit 9 at a position where a state in which the ultrasound probe 2 is in contact with the part of the subject corresponding to the acquired ultrasound image U can be easily confirmed. With this, with the ultrasound diagnosis apparatus 1 of Embodiment 1 of the invention, it is possible to allow the user to perform accurate diagnosis while referring to the ultrasound image U and the digital image D.

In addition, since the ultrasound image U and the digital image D saved in associated with each other by the save controller 10 as shown in FIG. 9 can be obtained, in a case of observing the ultrasound image U again after inspection on a specific subject ends, the user can refer to the digital image D where a state in which the ultrasound probe 2 is in contact with a part of the subject corresponding to the ultrasound image U can be easily confirmed. With this, it is possible to allow the user to easily confirm a part of the subject, with which the ultrasound probe 2 is brought into contact, in acquiring the ultrasound image U under observation.

In Embodiment 1, although the ultrasound image operation section 22 and the digital image operation section 23 are displayed on the display screen of the touch panel 8 and are operated when being touched by the user, the invention is not limited to this aspect. For example, though not shown, the ultrasound image operation section 22 and the digital image operation section 23 can be constituted of mechanical switches provided in the ultrasound diagnosis apparatus body B of the ultrasound diagnosis apparatus 1 shown in FIGS. 4 and 5. With this, for example, regions occupied by the ultrasound image operation section 22 and the digital image operation section 23 on the display screen of the touch panel 8 are allocated to a region where information of the subject is displayed, and the like, whereby it is possible to further secure the region where the ultrasound image U and the digital image D are displayed, and to allow the user to easily confirm the ultrasound image U and the digital image D.

In Embodiment 1, as shown in FIG. 7, although the digital image D is displayed in such a manner as to be superimposed on the ultrasound image U in a case where the digital image acquisition unit 9 is operated, the invention is not limited thereto. For example, though not shown, the digital image D can be displayed so as to completely replace the ultrasound image U freeze-displayed by a user's operation through the ultrasound image operation section 22. With this, since the digital image D is displayed in a greater region, the user easily confirms the digital image D. For example, though not shown, the ultrasound image U and the digital image D may be displayed in parallel such that the user views the whole images of the ultrasound image U freeze-displayed on the display screen of the touch panel 8 and the digital image D. With this, since the user can align the digital image acquisition unit 9 while confirming the freeze-displayed ultrasound image U, it is possible to obtain the more appropriate digital image D.

In Embodiment 1, in a case where digital image D is saved in association with the ultrasound image U, as shown in FIG. 8, the reduced digital image D is displayed in such a manner as to be superimposed the ultrasound image U displayed as a moving image; however, the user can be made to set whether or not to display the digital image D. For example, a digital image display erasure button (not shown) is displayed on the display screen of the touch panel 8, and the user can operate the digital image display erasure button, thereby setting such that erasure of the digital image D displayed in such a manner as to be superimposed on the ultrasound image U and re-display of the erased digital image D are performed. For example, the user may detach the ultrasound probe 2 from a body surface of the subject and may bring the ultrasound probe 2 into a so-called aerial radiation state, thereby setting such that the display of the digital image D displayed in such a manner as to be superimposed on the ultrasound image U is erased.

The save controller 10 can save the ultrasound image U and a time, at which the ultrasound image U is acquired, in association with each other, and can save the digital image D and a time, at which the digital image D is acquired, in association with each other. Though not shown, in this case, after a plurality of ultrasound images U and a plurality of digital images D are acquired, a plurality of acquired ultrasound images U and a plurality of acquired digital images D can be displayed on the display screen of the touch panel 8 in a time series. For example, in a case where the ultrasound images U and the digital images D are saved for each inspection on the subject, as specific inspection is selected by the user through the touch panel 8, a plurality of ultrasound images U and a plurality of digital images D in the selected inspection are displayed on the display screen in a time series. With this, it is possible to allow the user to easily confirm the correspondence relationship between the ultrasound image U and the digital image D.

After the inspection using the ultrasound diagnosis apparatus 1 ends, in order to confirm a state of inspection again, the user may record the display performed on the display screen of the touch panel 8 during inspection in an external memory (not shown) or the like. In Embodiment 1, as shown in FIG. 8, the reduced digital image D is displayed in such a manner as to be superimposed on the ultrasound image U displayed as a moving image. With this, in a case where the user confirms the recorded display again, it is possible to allow the user to easily ascertain a part of the subject that is inspected by the user.

Embodiment 2

In Embodiment 1, although the save controller 10 saves the ultrasound image U freeze-displayed on the display screen of the touch panel 8 and the digital image D acquired by the digital image acquisition unit 9 during the freeze display of the ultrasound image U in association with each other, a method of associating the ultrasound image U and the digital image D with each other is not limited thereto. Here, the ultrasound diagnosis apparatus 1 of Embodiment 2 has the same configuration of the ultrasound diagnosis apparatus 1 of Embodiment 1 shown in FIG. 1.

The save controller 10 in Embodiment 2 can further save an ultrasound image U, which is newly acquired by the ultrasound image acquisition unit 21 until a digital image D is newly acquired after a digital image D is initially acquired by the digital image acquisition unit 9, in the image memory 11 in association with the digital image D, which is initially acquired by the digital image acquisition unit 9 during the freeze display of the ultrasound image U, in the same inspection.

Figure 10:
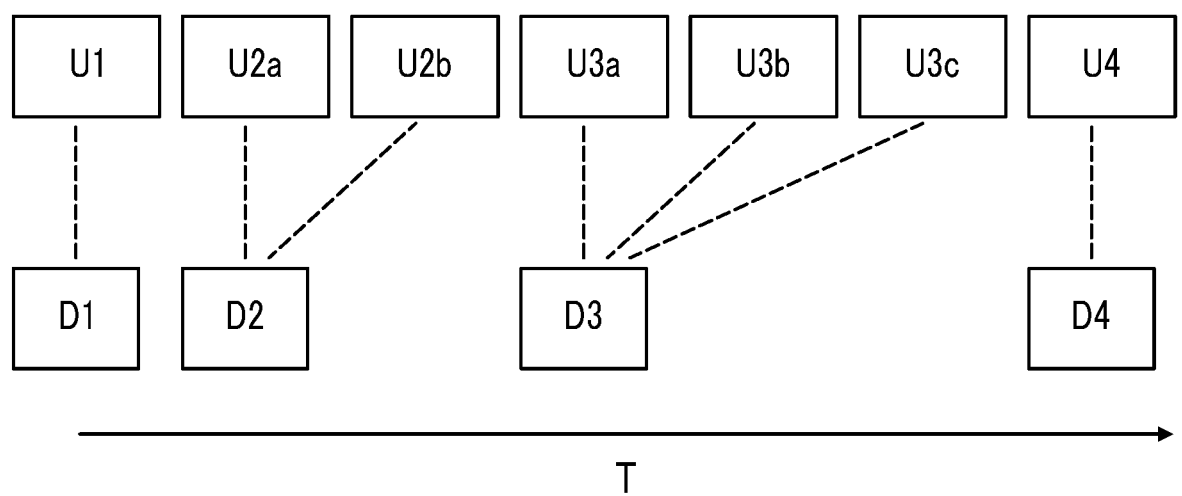
FIG. 10 is a conceptual diagram showing the correspondence relationship between an ultrasound image and a digital image associated with each other in Embodiment 2 of the invention.

Here, FIG. 10 is a conceptual diagram showing the correspondence relationship between the ultrasound image U and the digital image D associated with each other by the save controller 10 in Embodiment 2. In FIG. 10, U1, U2$a$, U2$b$, U3$a$, U3$b$, U3$c$, and U4 indicate ultrasound images stored in the image memory 11, D1 indicates a digital image associated with the ultrasound image U1, D2 indicates a digital image associated with the ultrasound images U2$a$ and U2$b$, D3 indicates a digital image associated with the ultrasound images U3$a$, U3$b$, and U3$c$, and D4 indicates a digital image associated with the ultrasound image U4. The ultrasound images U1, U2$a$, U2$b$, U3$a$, U3$b$, U3$c$, and U4 and the digital images D1, D2, D3, and D4 are arranged along an imaging time T.

The correspondence relationship between the ultrasound image U1 and the digital image D1 shown in FIG. 10 can be obtained, for example, by acquiring the digital image D1 with the digital image acquisition unit 9 during the freeze display of the ultrasound image U1 on the display screen of the touch panel 8 similarly to the method in Embodiment 1. The correspondence relationship between the ultrasound images U2$a$ and U2$b$ and the digital image D2 shown in FIG. 10 is obtained, for example, by acquiring the digital image D2 during the freeze display of the ultrasound image U2$a$, and then, acquiring the ultrasound image U3$a$ instead of newly acquiring a digital image immediately after the ultrasound image U2$b$ is acquired.

The correspondence relationship between the ultrasound images U3$a$, U3$b$, and U3$c$ and the digital image D3 shown in FIG. 10 is obtained, for example, by acquiring the digital image D3 during the freeze display of the ultrasound image U3$a$, then, acquiring the ultrasound images U3$b$ and U3$c$ instead of newly acquiring a digital image immediately after the ultrasound image U3$b$ is acquired, and acquiring the ultrasound image U4, similarly to the method of obtaining the correspondence relationship between the ultrasound images U2$a$ and U2$b$ and the digital image D2.

As described above, with the save controller 10 in Embodiment 2, since an ultrasound image, which is acquired until a new digital image is acquired after a digital image is initially acquired is saved in association with the digital image, which is initially acquired, in the same inspection, it is possible to easily associate a digital image with all ultrasound images acquired in the same inspection. With this, it is possible to allow the user to reduce effort in saving the ultrasound images and the digital images in association with each other, and to allow the user to observe the ultrasound images while confirming a state in which the ultrasound probe 2 is to contact with a part of the subject for all ultrasound images acquired in the same inspection.

Embodiment 3

In Embodiment 1, although the digital image D acquired by the digital image acquisition unit 9 is saved in the image memory 11 as it is in association with the ultrasound image U acquired by the ultrasound image acquisition unit 21, the digital image D may be processed at the time of association with the ultrasound image U.

Figure 11:
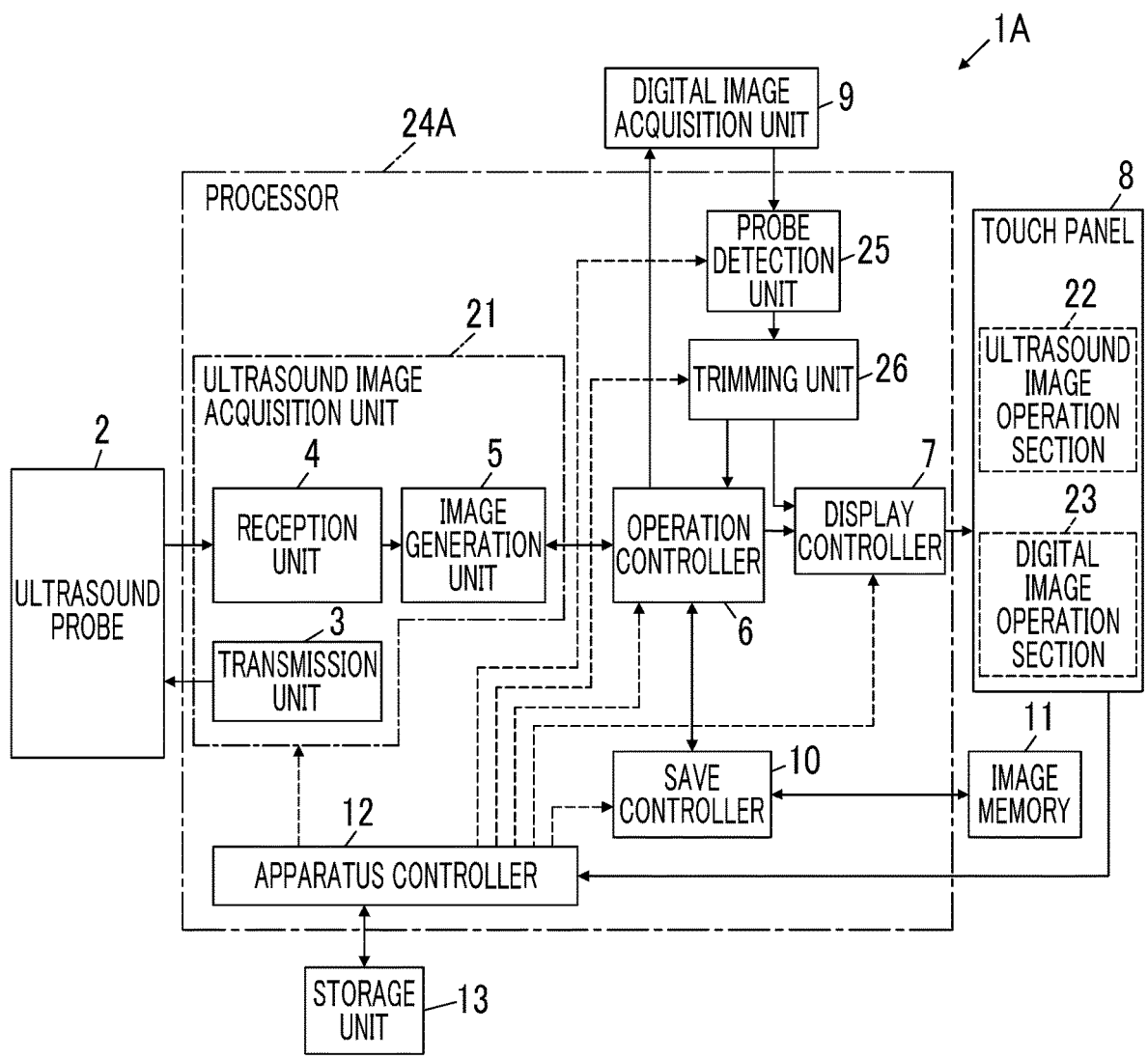
FIG. 11 is a block diagram showing the configuration of an ultrasound diagnosis apparatus according to Embodiment 3 of the invention.

FIG. 11 shows the configuration of an ultrasound diagnosis apparatus 1A of Embodiment 3. In the ultrasound diagnosis apparatus 1A of Embodiment 3, a probe detection unit 25 is connected to the digital image acquisition unit 9, a trimming unit 26 is connected to the probe detection unit 25, and the operation controller 6 and the display controller 7 are connected to the trimming unit 26. The apparatus controller 12 is connected to the probe detection unit 25 and the trimming unit 26. The operation controller 6, the display controller 7, the save controller 10, the apparatus controller 12, the ultrasound image acquisition unit 21, the probe detection unit 25, and the trimming unit 26 constitute a processor 24A. Here, the ultrasound diagnosis apparatus 1A of Embodiment 3 has the same configuration as the ultrasound diagnosis apparatus 1 of Embodiment 1 shown in FIG. 1, excluding that the probe detection unit 25 and the trimming unit 26 are provided.

The probe detection unit 25 of the processor 24A detects a position of the ultrasound probe 2 based on the digital image D acquired by the digital image acquisition unit 9. For example, the probe detection unit 25 can detect the position of the ultrasound probe 2 based on color information of the digital image D. The trimming unit 26 of the processor 24A generates a trimmed image obtained by cutting a peripheral portion of the position of the ultrasound probe 2 detected by the probe detection unit 25 from the digital image D.

Figure 12:
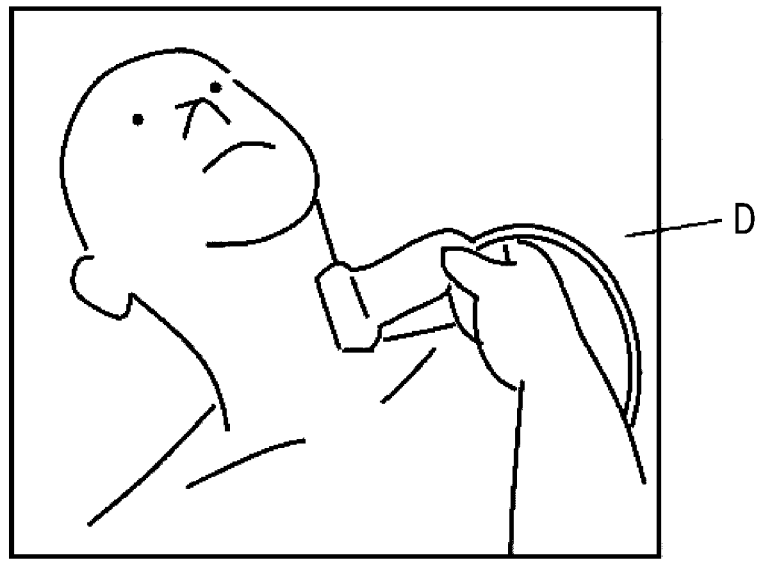
FIG. 12 is a diagram showing an example of a digital image captured in Embodiment 3 of the invention.
Figure 13:
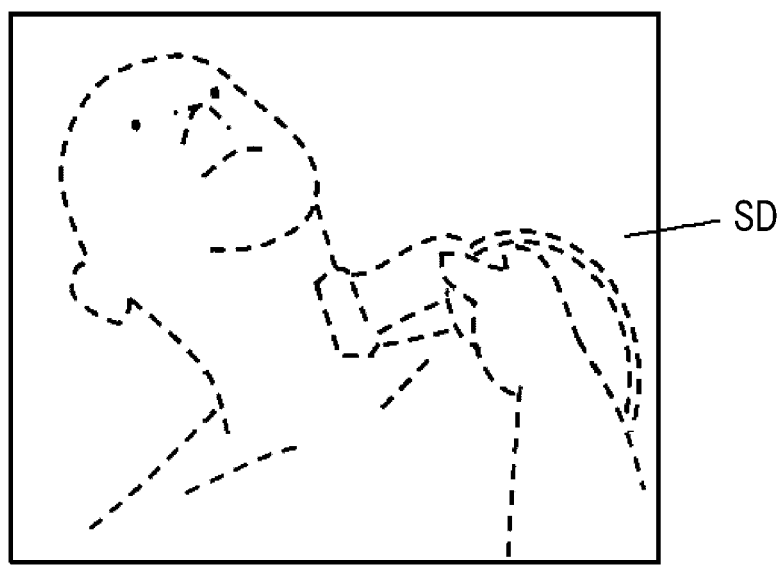
FIG. 13 is a conceptual diagram showing a state of image analysis on the digital image in Embodiment 3 of the invention.
Figure 14:
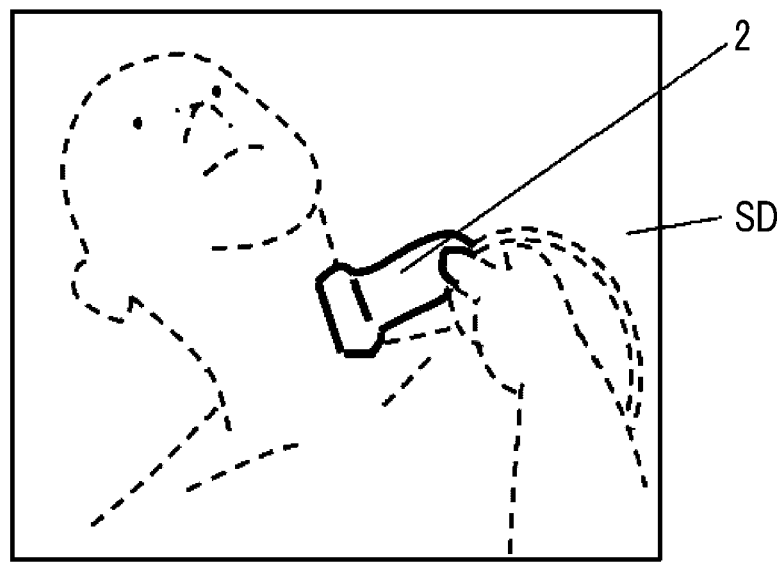
FIG. 14 is a conceptual diagram showing a state in which an ultrasound probe is detected in Embodiment 3 of the invention.

Next, an operation in generating the trimmed image in the ultrasound diagnosis apparatus 1A of Embodiment 3 will be described referring to FIGS. 12 to 16. First, in a case where a digital image D shown in FIG. 12 is acquired by the digital image acquisition unit 9, the position of the ultrasound probe 2 is detected based on the digital image D by the probe detection unit 25. For example, specifically, in detecting the position of the ultrasound probe 2 from the digital image D shown in FIG. 12, first, in order to smooth an edge portion included in the digital image D, as shown in FIG. 13, the probe detection unit 25 executes shading processing on the entire digital image D to obtain a shaded image SD. In this case, the probe detection unit 25 applies a so-called Gaussian filter or the like to the digital image D, thereby being able to shade off the entire digital image D. Next, as shown in FIG. 14, the probe detection unit 25 can detect a region, which has a preset range of chromaticity as a color of the ultrasound probe 2 and has a prescribed area or more, as the position of the ultrasound probe 2 for the shaded image SD.

Figure 15:
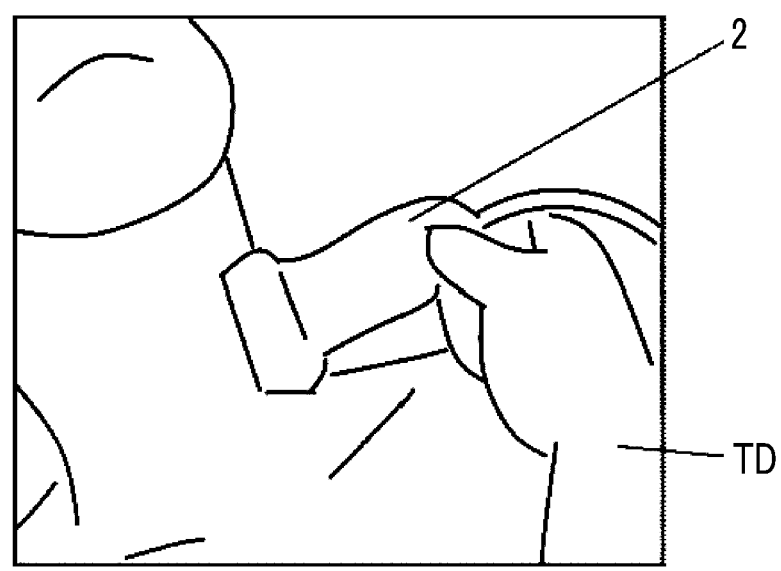
FIG. 15 is a diagram showing an example of a trimmed image in Embodiment 3 of the invention.

In a case where the position of the ultrasound probe 2 in the digital image D is detected by the probe detection unit 25, as shown in FIG. 15, the trimming unit 26 generates the trimmed image TD obtained by cutting the peripheral portion of the position of the ultrasound probe 2 from the digital image D. In this case, for example, the trimming unit 26 performs pattern matching on a shape of the ultrasound probe 2 detected by the probe detection unit 25 to discriminate a direction of the ultrasound probe 2 reflected in the digital image D, thereby being able to a position where the ultrasound probe 2 is in contact with the subject and cut a peripheral portion of the recognized position from the digital image D.

Figure 16:
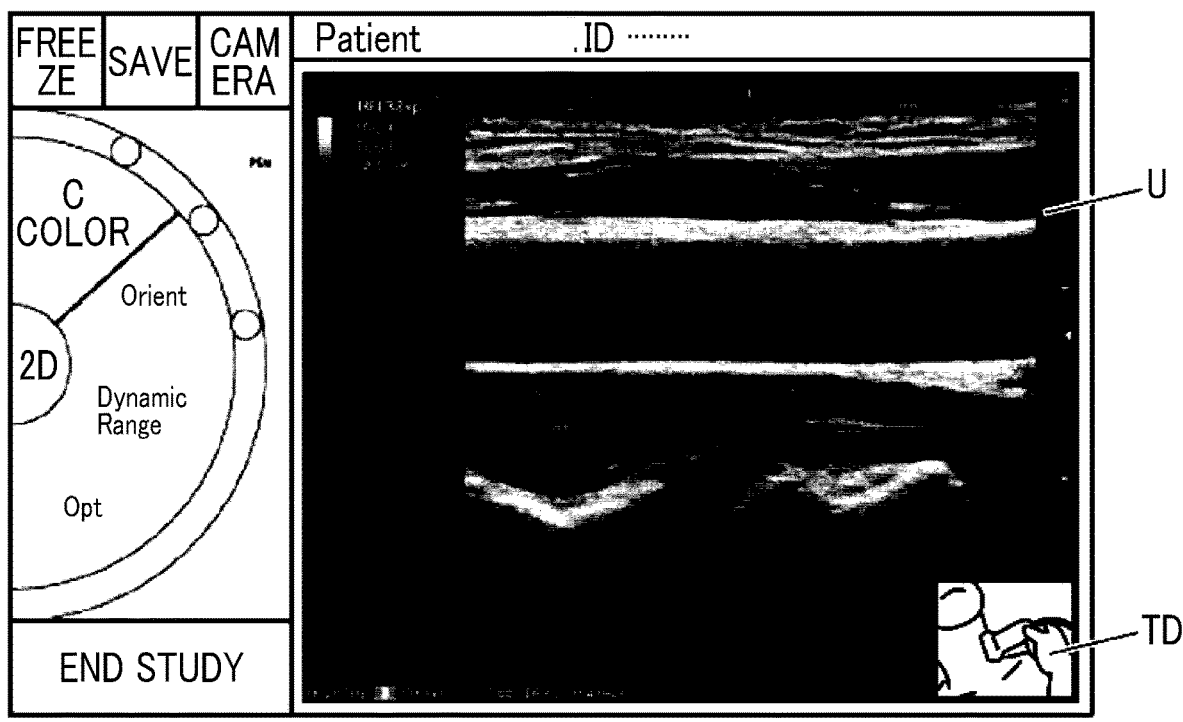
FIG. 16 is a diagram showing an example where the trimmed image is displayed in such a manner as to be superimposed on an ultrasound image in Embodiment 3 of the invention.

The trimmed image TD generated in this way is saved as the digital image D in association with the ultrasound image U by the save controller 10. As shown in FIG. 16, the trimmed image TD can be reduced and displayed in such a manner as to be superimposed on the ultrasound image U, similarly to the digital image D in Embodiment 1.

As described above, with the ultrasound diagnosis apparatus 1A in Embodiment 3, the trimmed image TD obtained by trimming the digital image D acquired by the digital image acquisition unit 9 can be generated, and the trimmed image TD can be saved as the digital image D in association with the ultrasound image U. Thus, when the user observes the ultrasound image U, it is possible to more clearly show the user a specific position where the ultrasound probe 2 is in contact with the subject.

Figure 17:
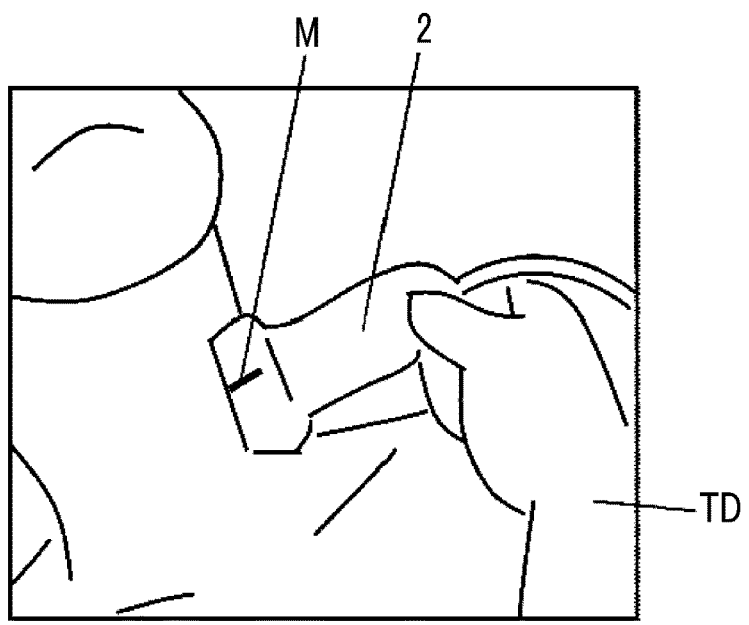
FIG. 17 is a diagram showing another example of a trimmed image in Embodiment 3 of the invention.

Although the trimming unit 26 uses pattern matching on the shape of the detected ultrasound probe 2 in trimming the digital image D, the invention is not limited to this aspect. For example, as shown in FIG. 17, in a case where the ultrasound probe 2 has a center mark M, the trimming unit 26 can discriminate the direction of the ultrasound probe 2 by recognizing a position of the center mark M of the ultrasound probe 2. The trimming unit 26 discriminates the direction of the ultrasound probe 2 in this way, thereby being able to recognize the position where the ultrasound probe 2 is in contact with the subject and cut the peripheral portion of the recognized position from the digital image D.

Embodiment 4

In general, in order that the user determines a part of the subject, with which the ultrasound probe 2 is in contact, in acquiring the ultrasound image U, a body mark and a probe mark may be attached to the ultrasound image U. Here, the body mark is a figure modeled on a part of the subject, and the probe mark is a figure modeled on the ultrasound probe 2 in order to indicate the direction and the position of the ultrasound probe 2. In the invention, the body mark and the probe mark can be automatically attached to the ultrasound image U based on the acquired digital image D.

Figure 18:
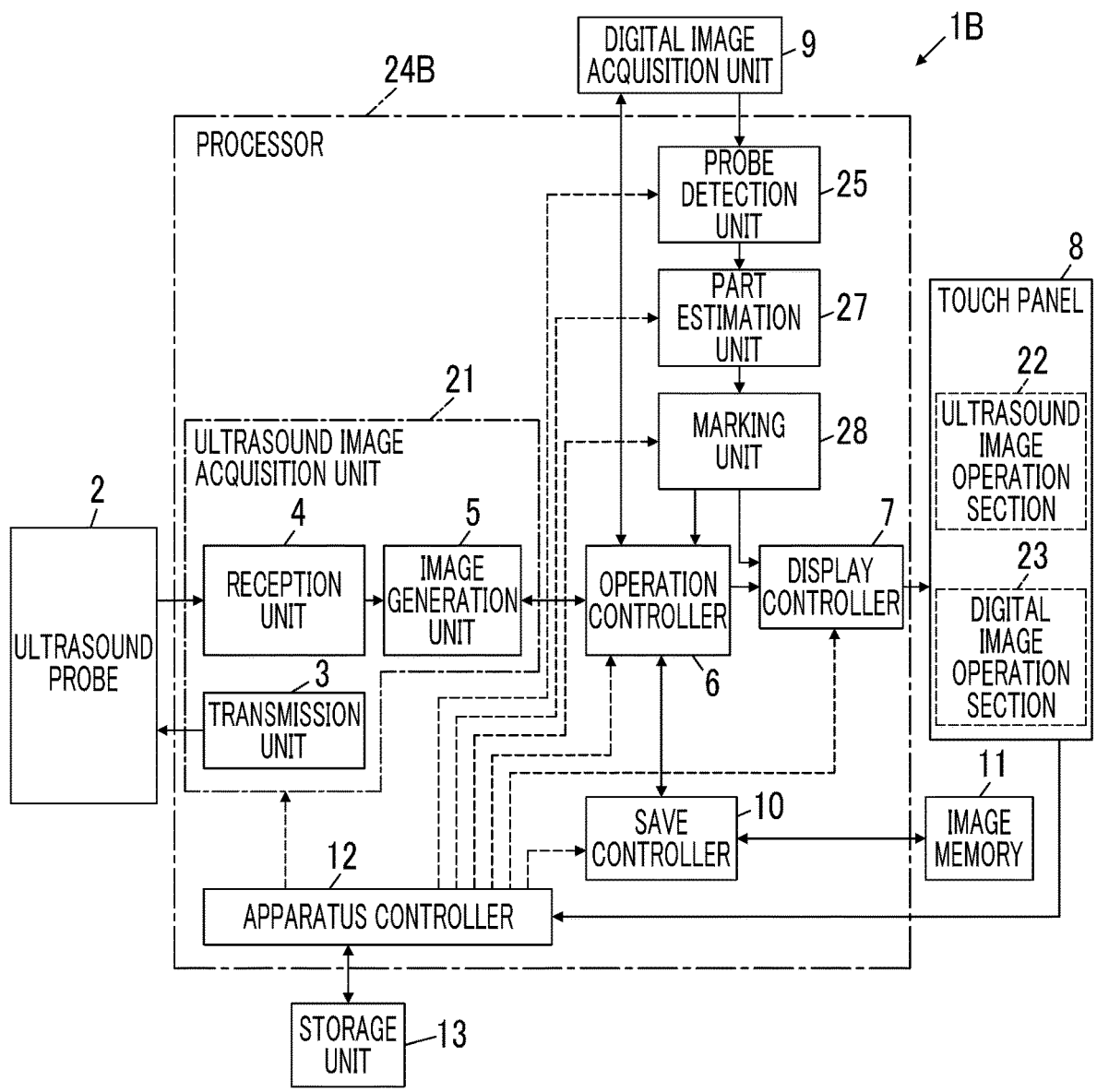
FIG. 18 is a block diagram showing the configuration of an ultrasound diagnosis apparatus according to Embodiment 4 of the invention.

As shown in FIG. 18, in an ultrasound diagnosis apparatus 1B of Embodiment 4, the probe detection unit 25 is connected to the digital image acquisition unit 9, a part estimation unit 27 is connected to the probe detection unit 25, and a marking unit 28 is connected to the part estimation unit 27. The operation controller 6 and the display controller 7 are connected to the marking unit 28. The apparatus controller 12 is connected to the probe detection unit 25, the part estimation unit 27, and the marking unit 28. The operation controller 6, the display controller 7, the save controller 10, the apparatus controller 12, the ultrasound image acquisition unit 21, the probe detection unit 25, the part estimation unit 27, and the marking unit 28 constitute a processor 24B.

Here, the ultrasound diagnosis apparatus 1B of Embodiment 4 has the same configuration as the ultrasound diagnosis apparatus 1 of Embodiment 1 shown in FIG. 1, excluding that the probe detection unit 25, the part estimation unit 27, and the marking unit 28 are provided. The probe detection unit 25 in Embodiment 4 is the same as the probe detection unit 25 in Embodiment 3 shown in FIG. 11.

The part estimation unit 27 of the processor 24B estimates a part of the subject, for which the ultrasound image U is acquired, based on the digital image D acquired by the digital image acquisition unit 9. For example, the part estimation unit 27 detects a skin region from the digital image D based on the color information of the digital image D and estimates a part of the subject based on the detected skin region and the position of the ultrasound probe 2 detected by the probe detection unit 25. The marking unit 28 of the processor 24B automatically attaches a body mark corresponding to the part estimated by the part estimation unit 27 to the ultrasound image U.

Figure 19:
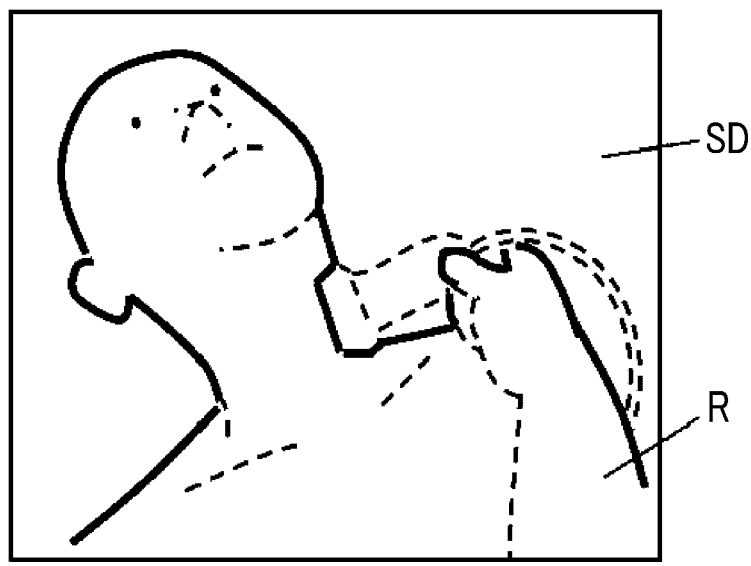
FIG. 19 is a conceptual diagram showing a state in which a skin region is detected in Embodiment 4 of the invention.
Figure 20:
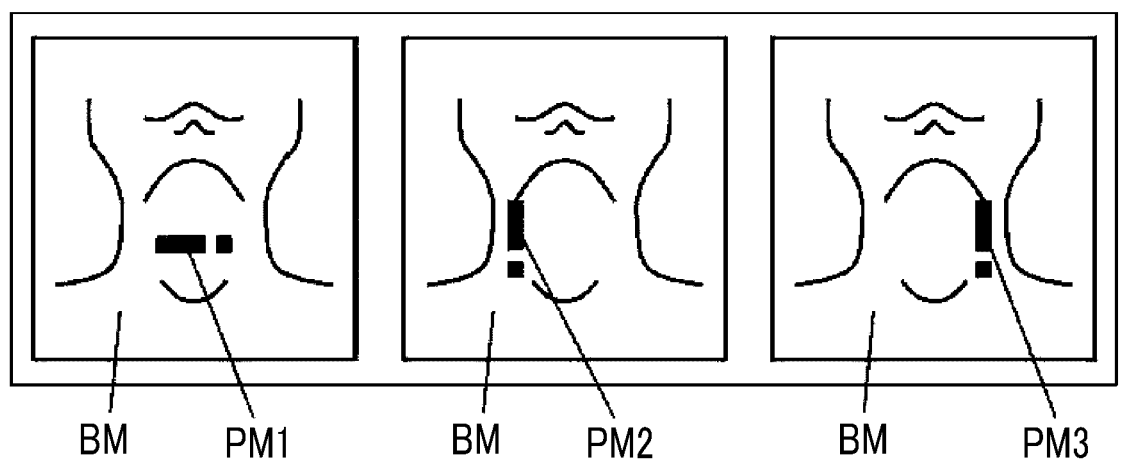
FIG. 20 is a diagram showing examples of a body mark of a cervical part and a probe mark in Embodiment 4 of the invention.
Figure 21:
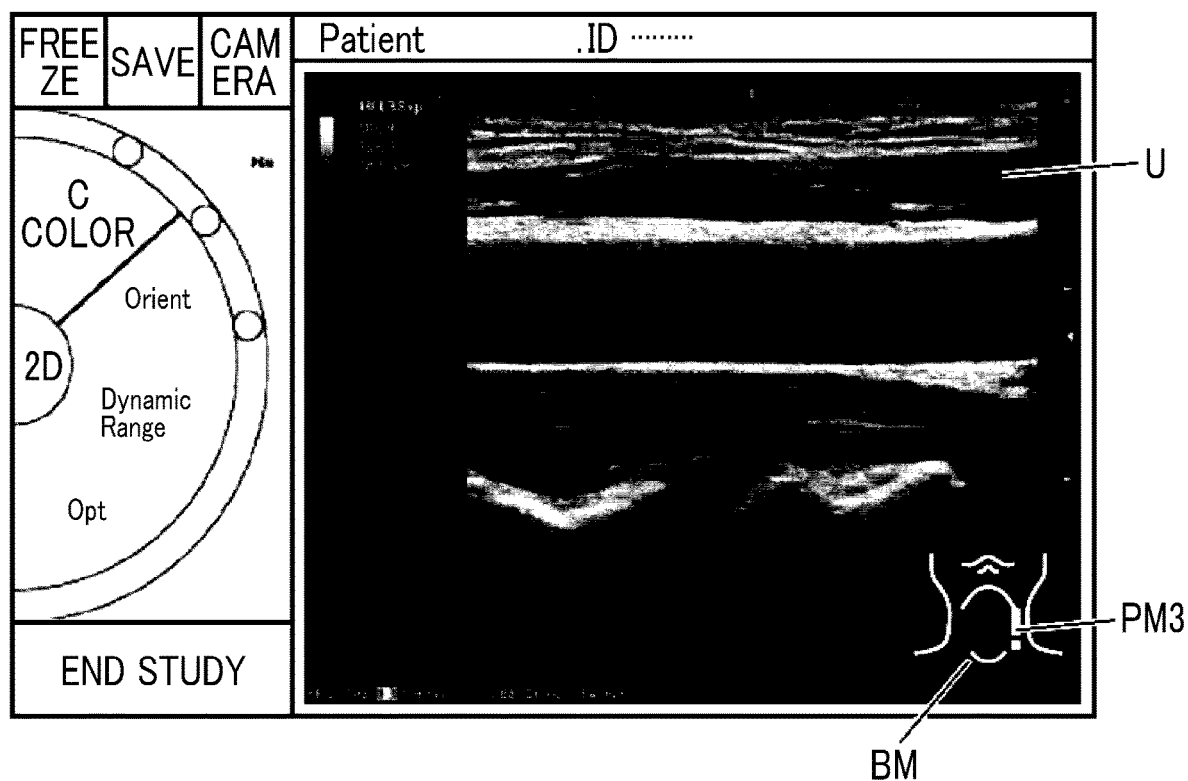
FIG. 21 is a diagram showing an example where the body mark and the probe mark are displayed in such a manner as to be superimposed on an ultrasound image in Embodiment 4 of the invention.

Next, an operation of the ultrasound diagnosis apparatus 1B in attaching the body mark and the probe mark to the ultrasound image U will be described referring to FIGS. 19 to 21. First, in a case where the digital image D indicating a state in which the ultrasound probe 2 is in contact with the part of the subject, is acquired by the digital image acquisition unit 9, the probe detection unit 25 detects the position of the ultrasound probe 2 from the digital image D as described in Embodiment 3.

In a case where the position of the ultrasound probe 2 in the digital image D is detected by the probe detection unit 25, the part estimation unit 27 detects the skin region based on the digital image D. For example, specifically, as shown in FIG. 19, the part estimation unit 27 can detect a region, which has a preset range of chromaticity as the color of skin and has a prescribed area or more, as a skin region R for the shaded image SD obtained by the probe detection unit 25.

The part estimation unit 27 estimates a part of the subject, with which the ultrasound probe 2 is in contact, based on the detected skin region R. In this case, the part estimation unit 27 performs pattern matching on the shape of the skin region R and estimates the part of the subject, with which the ultrasound probe 2 is in contact, using a result of pattern matching on the shape of the skin region R and the position of the ultrasound probe 2 detected by the probe detection unit 25. For example, in an example shown in FIG. 19, the part estimation unit 27 estimates the part, with which the ultrasound probe 2 is in contact, as a cervical part.

In this way, in a case where the part, with which the ultrasound probe 2 is in contact, is estimated by the part estimation unit 27, the marking unit 28 attaches a body mark and a probe mark to the ultrasound image U based on the estimated part. For example, in the example shown in FIG. 19, in a case where the part estimation unit 27 estimates that the part, with which the ultrasound probe 2 is in contact, is a cervical part, the marking unit 28 attaches a body mark representing the cervical part to the ultrasound image U.

The marking unit 28 can attach the probe mark along with the body mark based on the position of the ultrasound probe 2 detected by the probe detection unit 25. For example, in a case where the probe detection unit 25 detects that the ultrasound probe 2 is positioned in a left cervical part of the subject, as shown in FIG. 20, the marking unit 28 selects a probe mark PM3 indicating that the ultrasound probe 2 is positioned in the left cervical part among probe marks PM1, PM2, and PM3 stored in advance for a body mark BM of the cervical part. As shown in FIG. 21, the marking unit 28 attaches the probe mark PM3 selected in this way to the ultrasound image U along with the body mark BM of the cervical part.

In this way, in a case where the body mark and the probe mark are attached to the ultrasound image U by the marking unit 28, the save controller 10 saves the ultrasound image U along with the digital image D in association with the body mark and the probe mark.

As described above, with the ultrasound diagnosis apparatus 1B of Embodiment 4, since the body mark and the probe mark can be automatically attached to the ultrasound image U based on the digital image D acquired by the digital image acquisition unit 9, it is possible to save the effort of the user for attaching the body mark and the probe mark to the ultrasound image U.

In Embodiment 4, although the part estimation unit 27 detects the skin region R in the digital image D using the preset range of chromaticity as the color of skin, the range of chromaticity to be set as the color of skin can be set by the user. For example, a plurality of kinds of ranges of chromaticity set as the color of skin are saved in a memory (not shown) or the like, and the user selects the range of chromaticity through the digital image operation section 23 or the like, thereby being able to set the range of chromaticity to be set as the color of skin. With this, the part estimation unit 27 can detect the skin region R corresponding to the color of skin of the subject and can estimate the part, with which the ultrasound probe 2 is in contact.

In Embodiment 4, although the part estimation unit 27 estimates the part, with which the ultrasound probe 2 is in contact, using the result of pattern matching on the skin region R and the position of the ultrasound probe 2 detected by the probe detection unit 25, the part estimation unit 27 may estimate the part, with which the ultrasound probe 2 is in contact, using only the result of pattern matching on the shape of the skin region R.

In the ultrasound diagnosis apparatus 1B of Embodiment 4, when inspection on the subject is started, an inspection part name may be input by the user through the touch panel 8. In this case, the part estimation unit 27 can estimate a part, with which the ultrasound probe 2 is in contact, in consideration of the inspection part name input by the user corresponding to inspection, in addition to the skin region R and the position of the ultrasound probe 2. For example, in a case where a cervical part is input as the inspection part name by the user, the part estimation unit 27 attaches the body mark BM of the cervical part to the ultrasound image U and attaches the probe mark to the ultrasound image U based on the result of pattern matching of the skin region R and the position of the ultrasound probe 2 detected by the probe detection unit 25. With this, it is possible to reduce a calculation load in the part estimation unit 27, and to reduce a time needed for estimating a part in the part estimation unit 27.

The part estimation unit 27 can estimate a part, with which the ultrasound probe 2 is in contact, in consideration of the ultrasound image U in addition to the skin region R and the position of the ultrasound probe 2. For example, the part estimation unit 27 performs image analysis, such as pattern matching, on the ultrasound image U, in addition to the skin region R and the position of the ultrasound probe 2, thereby estimating a part with which the ultrasound probe 2 is in contact. With this, it is possible to improve accuracy of estimating a part in the part estimation unit 27.

Although the marking unit 28 selects an optimum probe mark from probe marks stored in advance based on the part estimated by the part estimation unit 27 in attaching the probe mark to the ultrasound image U, the position and direction of the probe mark can be changed by a user's operation through the digital image operation section 23 or the like.

Similarly to the transmission unit 3, the reception unit 4, the image generation unit 5, the operation controller 6, the display controller 7, the save controller 10, and the apparatus controller 12, the probe detection unit 25, the trimming unit 26, the part estimation unit 27, and the marking unit 28 constituting the processor 24 may be incorporated partially or entirely in one CPU. As the CPU executes the operation program, the CPU functions as the probe detection unit 25, the trimming unit 26, the part estimation unit 27, and the marking unit 28.

From the above description, it is possible to ascertain an ultrasound diagnosis apparatus described in the following supplementary item 1.

Supplementary Item 1

An ultrasound diagnosis apparatus comprising:
an ultrasound probe;
an ultrasound image acquisition processor that performs transmission and reception of an ultrasonic beam from the ultrasound probe toward a subject and images a reception signal output from the ultrasound probe to acquire an ultrasound image;
a digital camera that images a state of the ultrasound probe being in contact with the subject to acquire a digital image;
a touch panel that has a display screen displaying the ultrasound image acquired by the ultrasound image acquisition processor and the digital image acquired by the digital camera, and has an ultrasound image operation button provided to allow a user to operate the ultrasound image acquisition processor and a digital image operation button provided to allow the user to operate the digital camera;
an operation control processor that makes the digital image operating button operable by the user only in a case where the ultrasound image is freeze-displayed and exclusively operates the ultrasound image acquisition processor and the digital camera based on operations of the ultrasound image operation button and the digital image operation button;
an image memory that stores the ultrasound image and the digital image; and
a save control processor that saves the ultrasound image and the digital image acquired in the same inspection in the image memory in association with each other,
in which the digital camera acquires the digital image in a visual field in a direction opposite to a direction, to which the display screen of the touch panel is directed.

Explanation of References 1, 1A, 1B: ultrasound diagnosis apparatus, 2: ultrasound probe, 3: transmission unit, 4: reception unit, 5: image generation unit, 6: operation controller, 7: display controller, 8: touch panel, 9: digital image acquisition unit, 10: save controller, 11: image memory, 12: apparatus controller, 13: storage unit, 14: amplification unit, 15: AD conversion unit, 16: signal processing unit, 17: DSC, 18: image processing unit, 21: ultrasound image acquisition unit, 22: ultrasound image operation section, 23: digital image operation section, 24, 24A, 24B: processor, 25: probe detection unit, 26: trimming unit, 27: part estimation unit, 28: marking unit, B: ultrasound diagnosis apparatus body, BM: body mark, C: camera button, D, D2, D3, D4: digital image, E: shutter button, F: freeze button, L: camera lens, M: center mark, P1: front surface, P2: rear surface, PM1, PM2, PM3: probe mark, R: skin region, S: storage button, SD: shaded image, T: time, TD: trimmed image, U, U1, U2, U2$a$, U2$b$, U3, U3$a$, U3$b$, U3$c$, U4: ultrasound image, V: video.

What is claimed is:

1. An ultrasound diagnosis apparatus comprising:
an ultrasound probe;
an ultrasound image acquisition processor that performs transmission and reception of an ultrasonic beam from the ultrasound probe toward a subject and images a reception signal output from the ultrasound probe to acquire an ultrasound image;
a digital camera that images a state of the ultrasound probe being in contact with the subject to acquire a digital image;
a touch panel that has a display screen displaying the ultrasound image acquired by the ultrasound image acquisition processor, the digital image acquired by the digital camera, an ultrasound image operation button provided to allow a user to operate the ultrasound image acquisition processor and a digital image operation button provided to allow the user to operate the digital camera, wherein the ultrasound image operation button includes a freeze button and a save button;
an operation control processor that makes the digital image operating button operable by the user only in a case where the ultrasound image is freeze-displayed and exclusively operates the ultrasound image acquisition processor and the digital camera based on operations of the ultrasound image operation button and the digital image operation button;
an image memory that stores the ultrasound image and the digital image; and
a save control processor that saves the ultrasound image and the digital image acquired in a same inspection in the image memory in association with each other,
wherein the digital camera acquires the digital image in a visual field in a first direction opposite to a second direction, wherein the display screen of the touch panel is directed in the second direction.

2. The ultrasound diagnosis apparatus according to claim 1,
wherein the ultrasound image operation button and the digital image operation button are displayed on the display screen of the touch panel.

3. The ultrasound diagnosis apparatus according to claim 2,
wherein the save control processor is further configured to save the ultrasound image in association with a time at which the ultrasound image is acquired and save the digital image in association with a time at which the digital image is acquired.

4. The ultrasound diagnosis apparatus according to claim 3,
wherein the save control processor is further configured to save the ultrasound image freeze-displayed on the display screen of the touch panel and the digital image acquired during the freeze display of the ultrasound image in association with each other.

5. The ultrasound diagnosis apparatus according to claim 3,
wherein the ultrasound image acquisition processor is further configured to detect a position of the ultrasound probe based on the digital image.

6. The ultrasound diagnosis apparatus according to claim 2,
wherein the save control processor is further configured to save the ultrasound image freeze-displayed on the display screen of the touch panel and the digital image acquired during the freeze display of the ultrasound image in association with each other.

7. The ultrasound diagnosis apparatus according to claim 2,
wherein the ultrasound image acquisition processor is further configured to detect a position of the ultrasound probe based on the digital image.

8. The ultrasound diagnosis apparatus according to claim 1,
wherein the save control processor is further configured to save the ultrasound image in association with a time at which the ultrasound image is acquired and save the digital image in association with a time at which the digital image is acquired.

9. The ultrasound diagnosis apparatus according to claim 8,
wherein the save control processor is further configured to save the ultrasound image freeze-displayed on the display screen of the touch panel and the digital image acquired during the freeze display of the ultrasound image in association with each other.

10. The ultrasound diagnosis apparatus according to claim 8,
wherein the ultrasound image acquisition processor is further configured to detect a position of the ultrasound probe based on the digital image.

11. The ultrasound diagnosis apparatus according to claim 1,
wherein the save control processor is further configured to save the ultrasound image freeze-displayed on the display screen of the touch panel and the digital image acquired during the freeze display of the ultrasound image in association with each other.

12. The ultrasound diagnosis apparatus according to claim 11,
wherein the save control processor is further configured to save an ultrasound image acquired in a period until a digital image is newly acquired by the camera further in association with the digital image acquired during the freeze display of the ultrasound image.

13. The ultrasound diagnosis apparatus according to claim 1,
wherein the ultrasound image acquisition processor is further configured to detect a position of the ultrasound probe based on the digital image.

14. The ultrasound diagnosis apparatus according to claim 13,
wherein the ultrasound image acquisition processor is further configured to detect the position of the ultrasound probe based on color information of the digital image.

15. The ultrasound diagnosis apparatus according to claim 13,
wherein the ultrasound image acquisition processor is further configured to
generate a trimmed image by cutting a peripheral portion of the position of the ultrasound probe from the digital image; and
the save control processor is further configured to save the trimmed image as the digital image in association with the ultrasound image.

16. The ultrasound diagnosis apparatus according to claim 13,
wherein the ultrasound image acquisition processor is further configured to:
estimate, based on the digital image, a part of the subject where the ultrasound image is acquired; and
attach a body mark corresponding to the part to the ultrasound image.

17. The ultrasound diagnosis apparatus according to claim 16,
wherein the ultrasound image acquisition processor is further configured to attach a probe mark to the ultrasound image along with the body mark based on the position of the ultrasound probe.

18. The ultrasound diagnosis apparatus according to claim 16,
wherein the ultrasound image acquisition processor is configured to estimate the part of the subject in consideration of at least one of an inspection part name input by the user corresponding to the inspection or the ultrasound image.

19. The ultrasound diagnosis apparatus according to claim 16,
wherein the ultrasound image acquisition processor is configured to detect a skin region from the digital image based on color information of the digital image and estimate the part of the subject based on the detected skin region and the position of the ultrasound probe.

20. The ultrasound diagnosis apparatus according to claim 1,
wherein the ultrasound image acquisition processor is further configured to display the ultrasound image as a moving image on the display screen of the touch panel.

21. The ultrasound diagnosis apparatus according to claim 1,
wherein the ultrasound image acquisition processor is further configured to display the ultrasound image as a freeze image on the display screen of the touch panel in response to an operation of the ultrasound image operation button.

22. The ultrasound diagnosis apparatus according to claim 1,
wherein the operation control processor is further configured to make the digital image operation button operable by the user only in case where the ultrasound image is freeze-displayed in response to the operation of the ultrasound image operation button.

* * * * *